United States Patent [19]

Boesten et al.

[11] 4,371,464
[45] Feb. 1, 1983

[54] DIPEPTIDE SWEETENER

[75] Inventors: Wilhelmus H. J. Boesten, Sittard; Lambertus A. C. Schiepers, Maastricht, both of Netherlands

[73] Assignee: Stamicarbon, B.V., Geleen, Netherlands

[21] Appl. No.: 298,521

[22] Filed: Sep. 1, 1981

[30] Foreign Application Priority Data

Sep. 4, 1980 [NL] Netherlands .......................... 8005006

[51] Int. Cl.$^3$ ...................... C07C 103/52; A61K 37/00
[52] U.S. Cl. ................................ 260/112.5 R; 424/177
[58] Field of Search .................. 260/112.5 R; 424/177

[56] References Cited

U.S. PATENT DOCUMENTS

| | | | |
|---|---|---|---|
| 3,492,131 | 1/1970 | Schlatter | 260/112.5 R |
| 3,642,491 | 2/1972 | Schlatter | 260/112.5 R |
| 3,879,372 | 4/1975 | Boesten | 260/112.5 R |
| 4,029,701 | 6/1977 | Haas et al. | 260/112.5 R |
| 4,031,258 | 6/1977 | Haas et al. | 260/112.5 R |

OTHER PUBLICATIONS

Robert A. Mazur et al., *J. of Am. Chem. Soc.*, 91, 2684–2691 (1961).

*Primary Examiner*—Delbert R. Phillips
*Assistant Examiner*—F. T. Moezie

[57] ABSTRACT

Novel sweetener compounds having the formula:

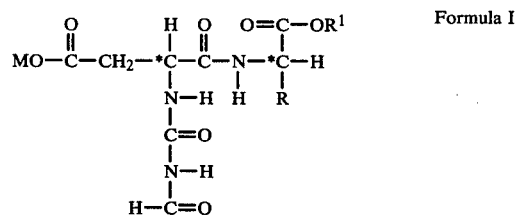

Formula I wherein
M represents hydrogen, ammonium, alkali or alkaline earth,
R represents

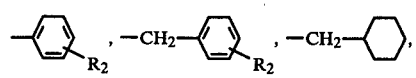

$R_1$ represents methyl, ethyl, or propyl,
$R_2$ represents —OH, or —OCH$_3$,
\* signifies an L-optical configuration for this atom.

3 Claims, 4 Drawing Figures

DIPEPTIDE SWEETENER

The invention relates to novel dipeptide sweeteners and to sweetening preparations based on these compounds. In particular, it pertains to novel N-(N'-formyl)-carbamyl protected dipeptide sweetners.

Dipeptide sweeteners known in the aret include L-alpha-aspartyl-L-phenylalaninemethylester, L-alpha-aspartyl-L-phenylglycinemethylester and L-alpha-aspartyl-L-beta-cyclohexylalaninemethylester. These dipeptide sweeteners have the disadvantage that they can form diketopiperazine derivatives.

In the literature it has been stated that only such unprotected dipeptides have the characteristic of being sweet to the taset. (See Journal of Medicinal Chemistry 1970, Vol. 13, No. 6, page 1217 and Ibid 1980, Vol. 23, No. 4, page 420).

The purpose of the present invention is to provide dipeptide sweeteners which cannot form diketopiperazine derivatives, and which are N-formylcarbamyl amino group protected dipeptides, i.e. dipeptides having an N-formylcarbamyl group.

Essentially these compounds are dipeptides in which the otherwise-free amino group has been converted into a formylcarbamyl group.

Thus, it has now been found according to this invention that compounds having the formula I, below, are, in fact, excellent sweeteners for human consumption.

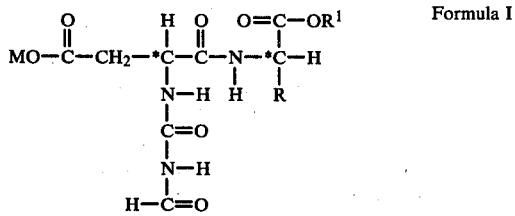

Formula I wherein:
M represents a hydrogen, ammonium, alkali-, or alkaline earth metal ion;
R represents

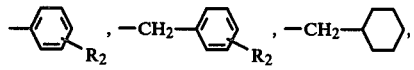

$R_1$ represents methyl, ethyl, or propyl,
$R_2$ represents —OH, or —OCH$_3$,
* signifies an L optical configuration for this atom.

It has been found from organoleptic research that these compounds are just about as sweet as are the alreay known uprotected sweeteners.

In the Journal Med. Chemistry, Vol. 23, page 420 (1980) and Vol. 13, page 1217 (1970) it is stated that the unsubstituted amino group of aspartic acid is necessary for the sweetness of dipeptides made therefrom.

It is therefore quite surprising that the N- (N'-formyl)-carbamyl protected dipeptides described herein are themselves sweet products.

The significant advantage of the amino group, or N-protected dipeptide sweeteners and their salts is that these N-protected dipeptide sweeteners cannot form diketopiperazine derivatives. Hence, these new N-protected dipeptide sweeteners are more stable, and there is no loss of sweetening power by the formation of diketopiperazine derivatives which are not sweet.

These new compounds, provided according to this invention, can be obtained by reacting the unprotected dipeptides with an alkali cyanate, and by then treating the resulting reaction product with the reaction product of acetic anhydride and formic acid. The N-(N'-formyl)-carbamyl derivatives can also be prepared by starting from N-(N'-formyl)-carbamyl aspartic anhydride, obtained by reacting aspartic acid with alkali cyanate and treating the thus obtained carbamyl compound with the reaction product of formic acid and acetic anhydride. The resulting N-(N'-formyl)-carbamyl aspartic anhydride can then also be reacted with an alkyl ester of the amino acid, whether or not in the form of salt, as described, for instance, in the U.S. Pat. No. 3,879,372, the disclosure of which is incorporated herein by reference. Examples are: the N'-formylcarbamyl derivatives of the lower alkyl (e.g., methyl, ethyl, propyl) esters of L-alpha-aspartyl-L-phenylalanine, L-alpha-aspartyl-L-phenylglycine, L-alpha-aspartyl-L-beta-cyclohexylalanine, L-alpha-aspartyl-L-tyrosine. N-(N'-formyl)-carbamyl-L-alpha-aspartyl-L-phenylalanine-methylester is particularly advantageous on account of the good taste and the great sweetening power.

These N'-formylcarbamyl protected dipeptides can be employed as such or they may be processed further into a sweetening preparation, with, for instance, a pharmacologically acceptable carrier, such as in the form of tablets or solutions. These compounds can then also be employed as a sweetening product mixed with other sweeteners, such as saccharine and cyclamate, or with sugars such as fructose.

The preparation of the new sweeteners will now be elucidated by means of the following non-restrictive examples.

EXAMPLE I

In a flask (0.5 ) provided with a stirrer 8.5 g (0.029 Mol) L-alpha-aspartyl-L-phenylalanine-methylester was dissolved in a solution of 4.6 g (0.058 Mol) potassium cyanate in 100 ml water and subsequently stirred at room temperature for 24 hours. After that, the turbid suspension obtained was filtered and the filtrate thus obtained was acidified with HCl to a pH of 2 and subsequently evaporated at 30° C. and 12 mbar.

The deposit thereby obtained was incorporated into 250 ml isopropanol and evaporated again to dryness. This was repeated and the crystal mass thus obtained was then incorporated in 500 ml isopropanol and subsequently stirred for 1 hour. This suspension was then filtered for the purpose of removing the KCl, and the filtrate obtained was evaporated and dried. The product obtained (8.3 g; 0.025 Mol) was analyzed according to nuclear spin resonance (for spectra see FIG. 1) and infra-red analysis, and found to consist of N-carybamyl-L-alpha-aspartyl-L-phenyl-alaninemethylester. The yield was 85%.

This carbamyl compound 4 g (0.012 Mol) was dissolved, while being stirred at 25° C., in a mixture of 20 ml acetic anhydride and 100 ml formic acid. At this temperature, a reaction was effected for 18 hours, after which 3 ml water was added and the material subsequently evaporated to dryness.

The dry product was next incorporated in 100 ml diethyl ether and subsequently filtered. The solid product obtained was twice washed on the filter with 50 ml diethyl ether and subsequently dried.

The product 3.5 g (0.0096 Mol) obtained consisted of N-(N'-formyl)-carbamyl-L-alpha-aspartyl-L-phenylalaniemethylester according to nuclear spin resonance (for Spectra see FIGS. 2, 3 and 4), mass spectrometry and infra-red analysis. The yield was 80%.

It was next found, from organoleptic research, that this compound was 200 times sweeter than sucrose. No difference in this regard could be established with respect to the unprotected sweetener L-alpha-aspartyl-L-phenylalanienemethylester.

EXAMPLE II

Figure 1:
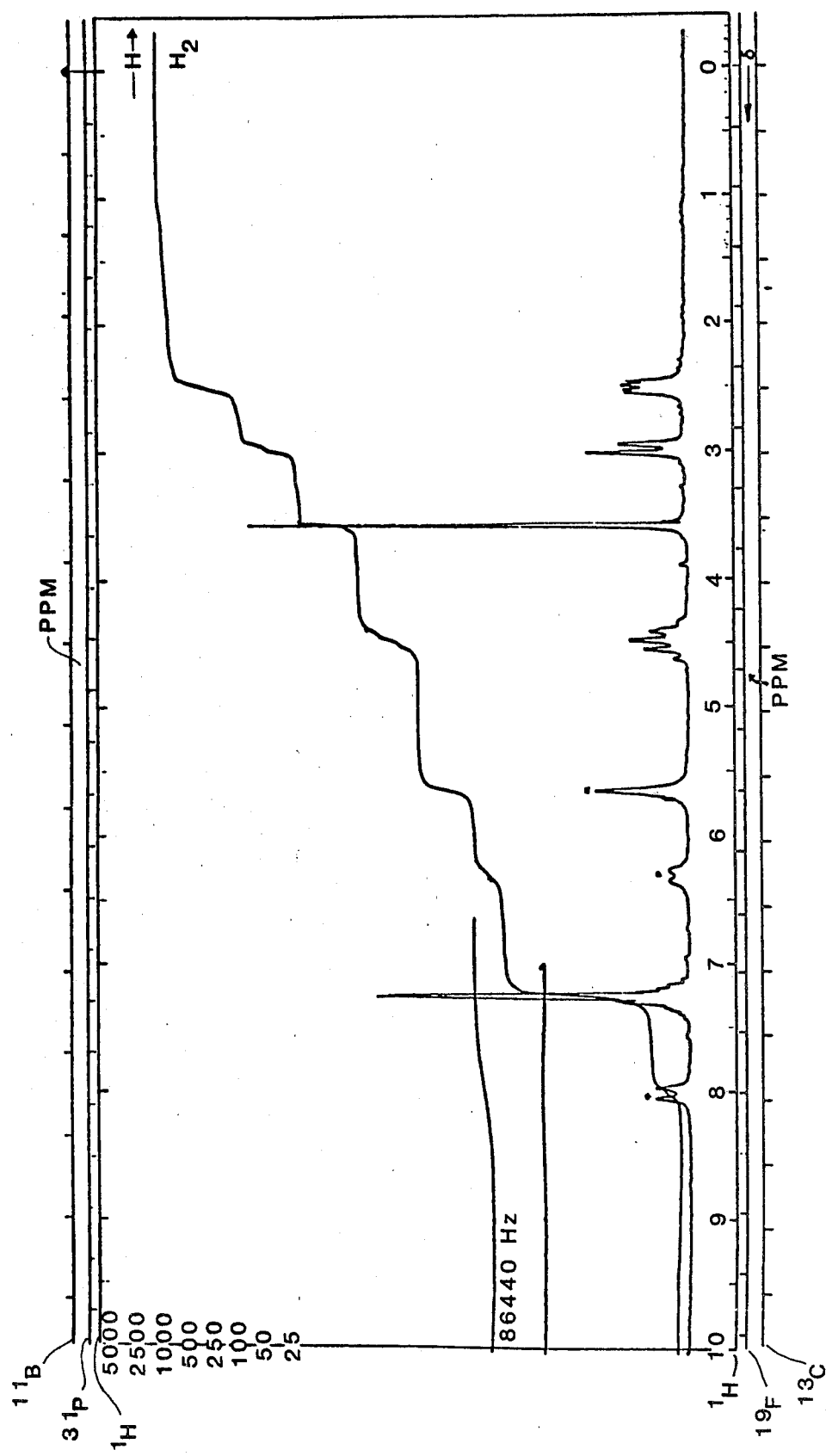
FIG. 1 is the 100 MHz $^1$H Spectrum of N-carbamyl-L-alpha-aspartyl-L-phenylalaninemethylester dissolved in DMSO d6.
Figure 2:
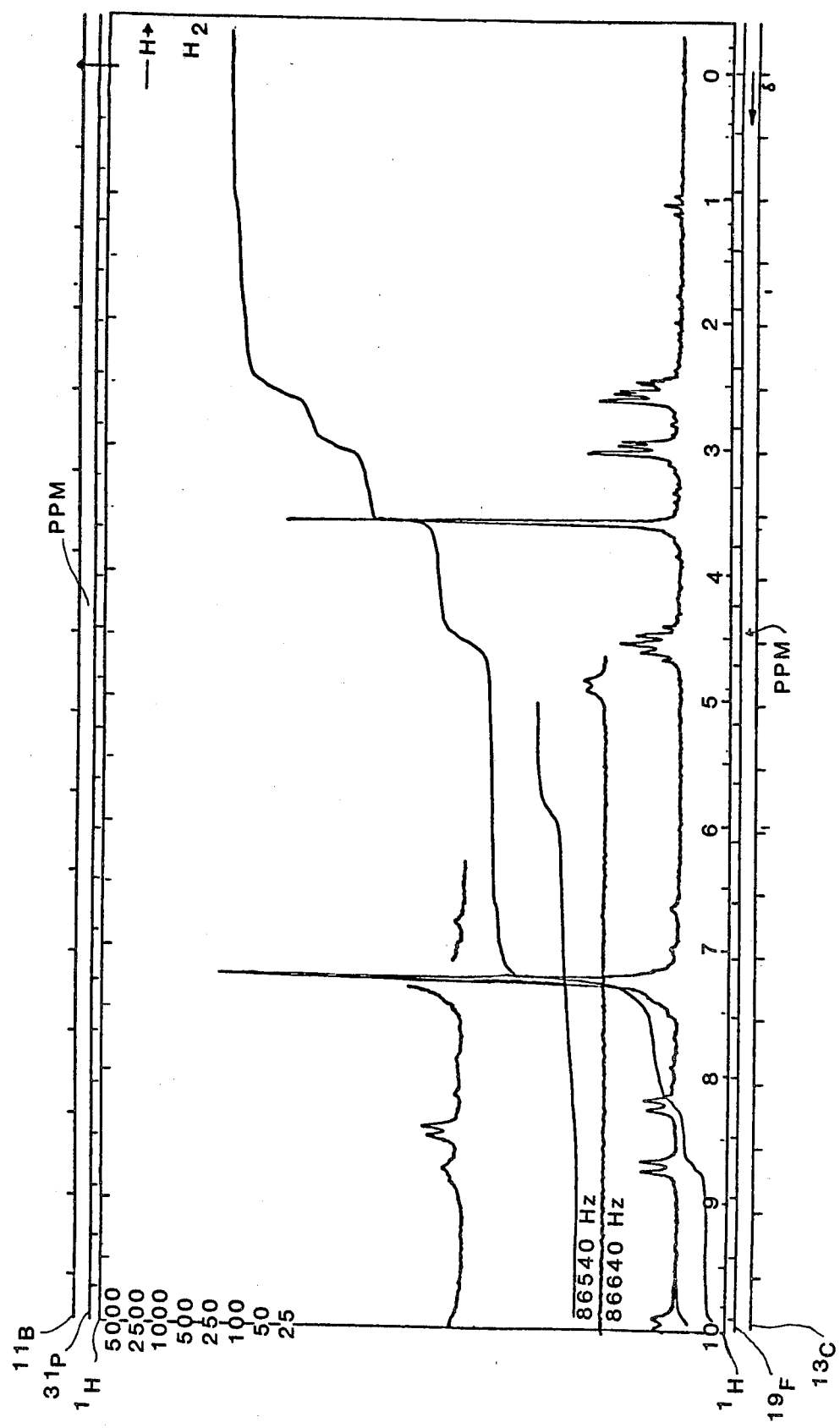
FIG. 2 is the 100 MHz $^1$H Spectrum of N-(N'-formyl)-carbamyl-L-alpha-aspartyl-L-phenylalaninemethylester dissolved in DMSO d6.
Figure 3:
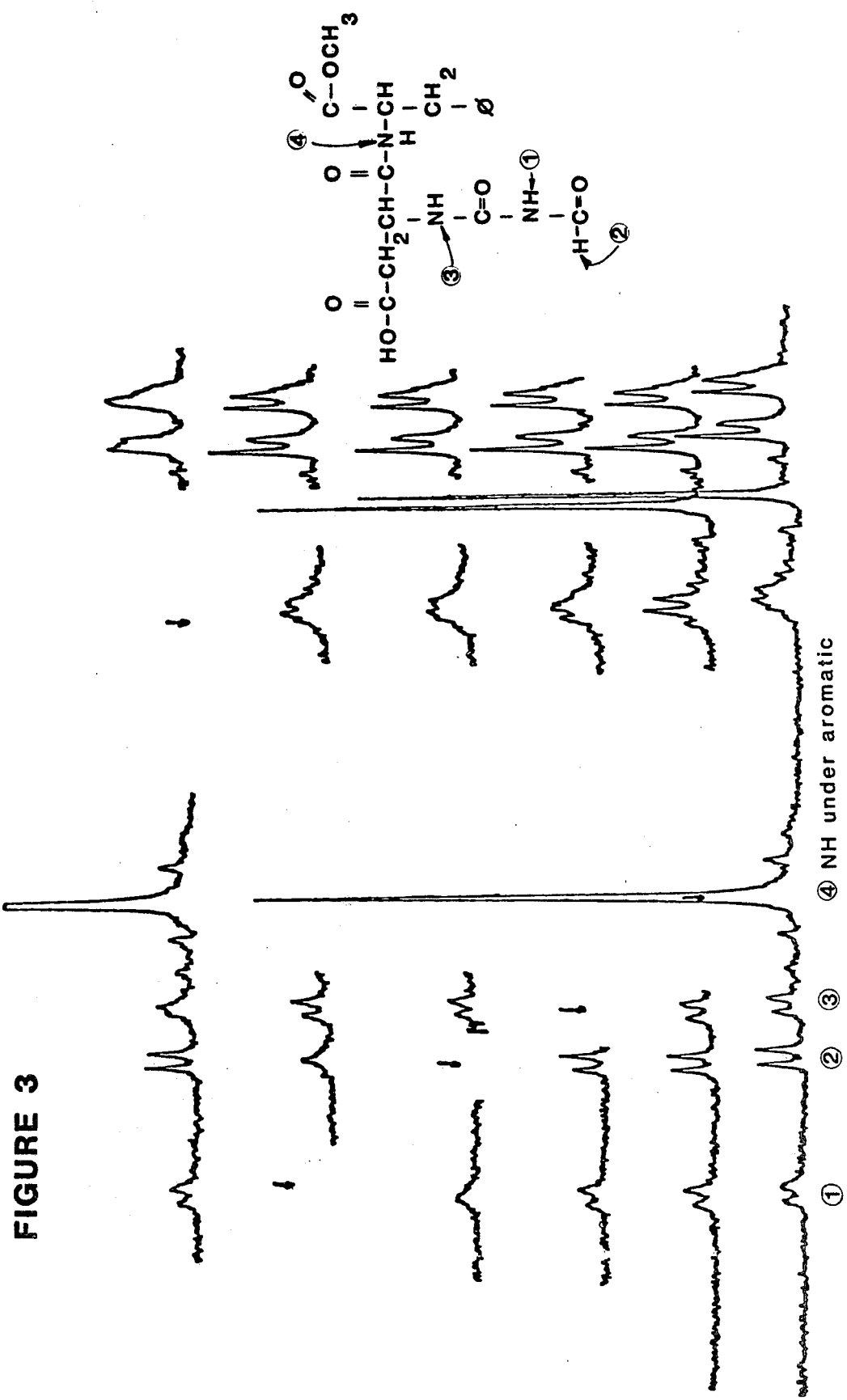
FIG. 3 shows the decoupling experiments at 60 MHz on N-(N'-formyl)-carbamyl-L-alpha-aspartyl-L-phenylalaninemethylester in DMSO d6, the irradiation frequencies having been indicated with arrows.
Figure 4:
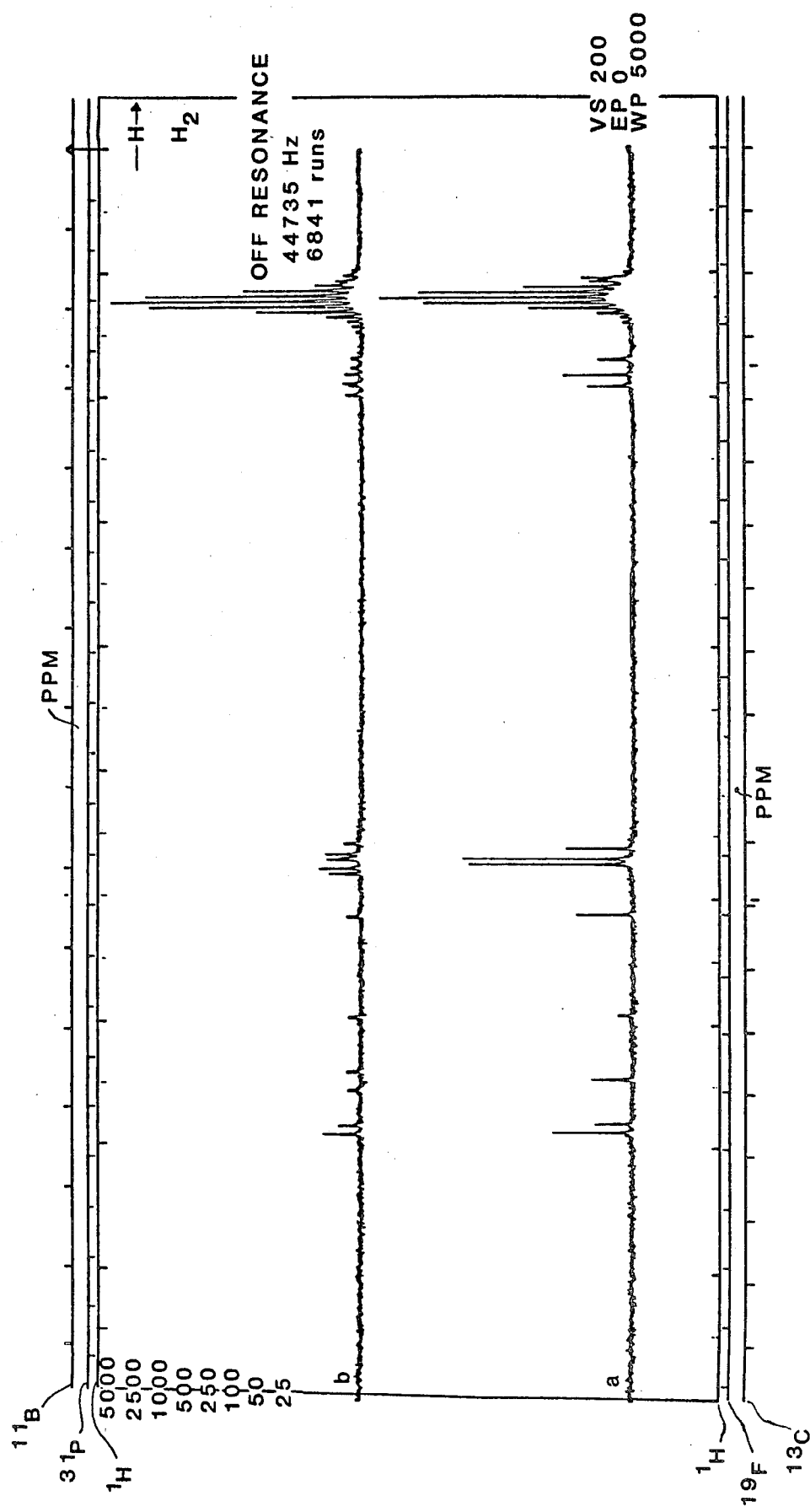
FIG. 4 is the 25.2 MHz $^{13}$C spectrum of N-(N'-formyl)-carbamyl-L-alpha-aspartyl-L-phenylalaninemethylester in DMSO d6, where a = $^1$H decoupled and b = not decoupled.

In a flask (0.5 l) provided with a stirrer 4.3 g (0.015 Mol) L-alpha-aspartyl-L-phenylglycine-methylester was suspended, while being stirred, into a solution of 2.49 g (0.03 Mol) potassium cyanate in 125 ml water. After reacting for 18 hours at 20° C., filtration was effected.

The filtrate was brought to a pH of 2 by acidification with HCl, in which process crystallization commenced. After stirring for 15 minutes, more filtration was carried out, and the crystal mass obtained was dried. A solid product 2.7 g was obtained which, according to nuclear spin resonance and infra-red analysis, contained N-carbamyl-L-alpha aspartyl-L-phenylglycinemethylester. By extraction of the filtrate, 5 times with 100 ml ethyl acetate, an additional 0.9 g of the carbamyl compound was obtained. The yield was 74%.

The N-carbamyl-L-alpha-aspartyl-L-phenylglycinemethylester (1.3 g 0.004 Mol) was incorporated in a mixture of 10 ml acetic anhydride and 50 ml formic acid, upon which the whole was stirred for 20 minutes more at 25° C. to dissolve everything. After reacting for 18 hours, 1.5 ml water was added, well stirred and subsequently evaporated to dryness at 30° C. and 12 mbar. The product obtained was next stirred with 25 ml diethyl ether and subsequently filtered. The crystal slurry was washed on the filter with 25 ml diethyl ether and subsequently dried.

A product (1.2 g) was obtained consisting, according to nuclear spin resonance, mass spectrometry and infra-red analysis, of N-(N'-formyl)-carbamyl-L-alpha-aspartyl-L-phenylglycinemethylester. The yield was 86%.

It was found from organoleptic research that this compound was 200 times sweeter than sucrose.

What is claimed is:

1. Compounds having the general formula

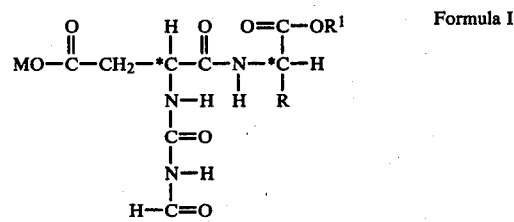

Formula I wherein
M represents hydrogen, ammonium, alkali or alkaline earth,
R respesents

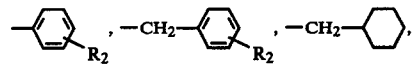

$R_1$ represents methyl, ethyl, or propyl,
$R_2$ represents —OH, or —OCH$_3$,
* signifies an L-optical configuration for this atom.

2. N-(N'-formyl)-carbamyl-L-alpha-aspartyl-L-phenylalaninemethylester.

3. N-(N'-formyl)-carbamyl-L-alpha-aspartyl-L-phenylglycinemethylester.

* * * * *